United States Patent [19]

Pegg et al.

[11] Patent Number: 4,826,968
[45] Date of Patent: May 2, 1989

[54] S-ALKYLATED COENZYME A WITH EFFECT ON POLYAMINE ACETYLASE

[75] Inventors: Anthony E. Pegg, Hummelstown; Bradley G. Erwin, Hershey, both of Pa.

[73] Assignee: Research Corporation, New York, N.Y.

[21] Appl. No.: 727,508

[22] Filed: Apr. 26, 1985

[51] Int. Cl.⁴ ............... C07H 19/167; C07H 19/207
[52] U.S. Cl. .................................. 536/27; 536/26; 536/28; 536/29; 530/331; 544/247
[58] Field of Search .................................. 536/25, 22

[56] References Cited

U.S. PATENT DOCUMENTS 2,917,434  12/1959  Robillant .................... 536/28

OTHER PUBLICATIONS

Erwin, B. G., Persson, L., Pegg, A. E., Biochemistry, vol. 23, pp. 4250–4255, 1984.

Primary Examiner—Ronald W. Griffin
Assistant Examiner—L. Eric Crane
Attorney, Agent, or Firm—Scully, Scott, Murphy & Presser

[57] ABSTRACT

The present invention relates to the novel compound N-[2-(S-Coenzyme A) acetyl] sym-norspermidine which electively inhibits the enzyme spermidine/spermine $N^1$ acetyl transferase thereby aberrating the polyamine biosynthesis pathway. The present compound alone or in combination with other agents can be employed in pharmaceutically acceptable compositions and in convenient dosage forms for use in the treatment of neoplastic diseases, diseases caused by parasitic protozoans, diseases involving deranged cell growth or other related diseases.

3 Claims, 2 Drawing Sheets

S-ALKYLATED COENZYME A WITH EFFECT ON POLYAMINE ACETYLASE

GOVERNMENT SUPPORT

The invention described herein was made in the course of work under a grant or award from the National Institute of Health of the Public Health Service (Research Grants GM-26290, 1P30 CA 18450 and CA 18138).

BACKGROUND OF THE INVENTION

The present invention relates to new compounds which are useful in the regulation of the interconversion of polyamines. More specifically, the present invention contemplates inhibitors of spermidine/spermine $N^1$-acetyltransferase, which plays a key role in regulating the interconversion of polyamines.

Maintenance of normal cellular polyamine concentration is needed for normal cell growth. When polyamine synthesis is prevented, cell growth is retarded, offering an opportunity to study the physiological role of the acetylase/oxidase pathway for the interconversion of polyamines. The inhibitors of polyamine synthesis have considerable potential as therapeutic agents for a wide variety of diseases. These inhibitors have their greatest potential when employed in the treatment of neoplastic diseases and other diseases involving deranged cell growth or as antiparasitic protozoan agents.

Ornithine decarboxylase is the only route to de novo polyamine synthesis in mammalian cells, but these cells are able to redistribute polyamines via the acetylase/oxidase pathway. The rate limiting step in this cellular redistribution is the spermidine/spermine $N^1$-acetyltransferase. The present compound is a specific and potent inhibitor of this enzyme, which can be used to prevent the acetylation step and subsequent redistribution of polyamines. This inhibitor, either alone or in combination with other compounds which affect other steps in the polyamine pathway, inhibits the production of specific enzymes in the pathway and therefore has wide potential in the treatment of various diseases.

Mammalian cells are known to contain a number of enzymes that catalyze the acetylation of polyamines and histones. Matsui, et al. (*J. Biol. Chem.* 256, 2454-2459, 1981) identified inducible spermidine/spermine $N^1$-acetyltransferase as an enzyme that catalyzes the acetylation of polyamines and plays a key role in the regulation of polyamine interconversion.

Cullis, et al. ("Inhibition of Histone Acetylation by N-[2-(S-Coenzyme A)Acetyl] Spermidine Amide, A Multisubstrate Analog," *J. Bio. Chem.*, Vol. 257, No. 20, pp. 12165-12169 (1982)) describe a method of synthesis of a multisubstrate analog N-[2-(S-Coenzyme A)acetyl] spermidine amide as a potential histone acetylation inhibitor. This research demonstrated the ability of this analog to inhibit histone acetylation in mammalian cells.

Further work done by Erwin, et al.("Differential Inhibition of History and Polyamine Acetylase by Multisubstrate Analogues," *Biochemistry* 23(18): pp 4250-4255, 1984) describes a method of synthesis similar to Cullis, et al. According to this study, interconversion of polyamines can be varied in response to exogenous stimuli.

Earlier, Libby, in a publication entitled, "Acetyl Spermidine Deacetylase," *Arch. Biochem. Biophys.*, Vol. 188, p. 360 (1978) described the results of the inhibition of the deacetylase enzyme by various polyamines.

A recent study by Sjoerdsma and Schechter ("Chemotherapeutic Implications of Polyamine Biosynthesis Inhibition," *Clin. Pharmacol. Therap.*, (1983)) discusses the clinical significance of polyamine biosynthesis in such diseases as neoplastic disease, parasitic protozoan caused diseases, diseases involving deranged cell growth and other related diseases. Specifically, the researchers tested the effects of D,L-difluoromethylornithine (DFMO) as an inhibitor of polyamine biosynthesis and its value as a therapeutic agent in various diseases. The results indicated that the therapeutic value of DFMO was minimal, but that an effective inhibitor would possess tremendous potential as a therapeutic agent.

SUMMARY OF THE INVENTION

It is therefore one object of the present invention to provide a novel compound which inhibits the interconversion of polyamines.

It is another object of this invention to provide a compound useful for the inhibition of the enzyme spermidine/spermine $N^1$-acetyltransferase, which catalyzes the conversion of spermine and spermidine.

Another object of the invention is to provide compounds useful in the treatment of neoplastic diseases, parasitic protozoan caused diseases, other diseases involving deranged cell growth and other related diseases.

These and other objects are achieved herein by providing the compound N-[2-(S-Coenzyme A)acetyl] sym-norspermidine amide which inhibits polyamine biosynthesis i.e., the specific inhibition of the enzyme spermidine/spermine $N^1$-acetyltransferase and histone acetylase. This inhibitory compound is prepared by attaching spermidine to Coenzyme A via an acetic acid linkage. The present invention contemplates employing the novel compound in combination with the other known inhibiting agents and/or in compositions of acceptable pharmaceutically active dosage forms. It is also within the scope of this invention to employ the present compound alone or in combination with other therapeutic agents for the treatment of neoplastic diseases, parasitic protozoan caused diseases, diseases caused by deranged cell growth and other related diseases. These methods are conveniently affected by the administration of an effective amount of N-[2-(S-Coenzyme A) acetyl] sym-norspermidine amide.

DETAILED DESCRIPTION OF THE INVENTION

Figure 1:
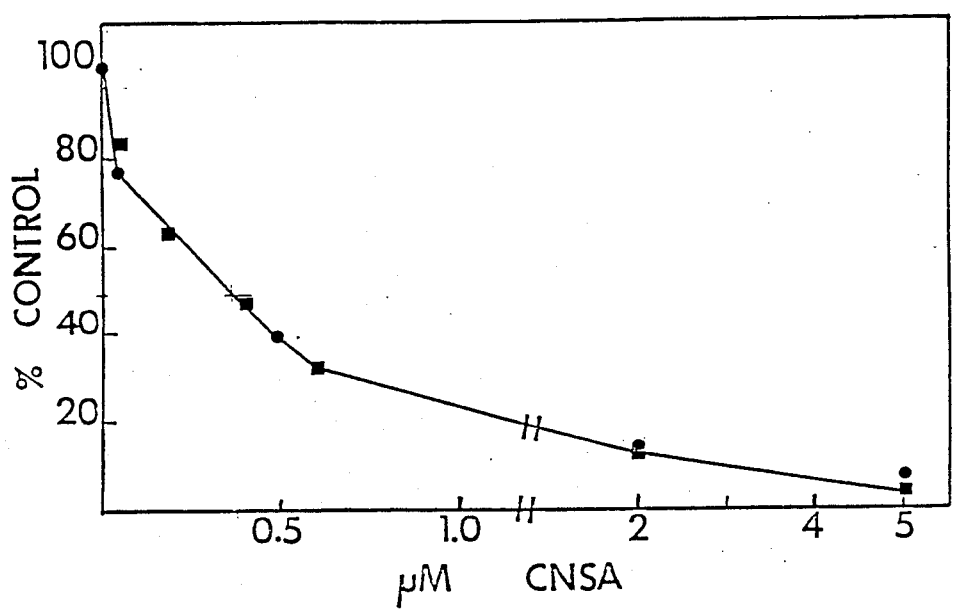
FIG. 1 is a graphic illustration depicting the inhibition of spermidine (Spermine $N^1$-acetyltransferase) by N-[2-(S-Coenzyme A) acetyl] sym-norspermidine amide (CNSA).

In accordance with the present invention it has been surprisingly discovered that N-[2-(S-Coenzyme A) acetyl] sym-norspermidine amide exhibits superior ability to inhibit the acetylation of spermidine or spermine. Since it has also been found that spermidine/spermine $N^1$-acetyl-transferase plays a key role in the regulation of the interconversion of polyamines, the novel compound of this invention is an effective inhibitor of polyamine interconversion and more significantly, has tremendous therapeutic value in the treatment of various diseases.

The present invention contemplates that N-[2-(S-Coenzyme A) acetyl] sym-norsperimidine amide in the combination with known cytotoxic compounds has therapeutic value in a method for treatment of neoplastic diseases, parasitic protozoan caused diseases, diseases involving deranged cell growth and other related diseases. By the term neoplastic disease is meant disease which is caused by any new or abnormal growth of tissue in which growth is uncontrolled and progressive whether benign or malignant.

The novel compound of the present invention, N-[2-(S-Coenzyme A) acetyl] sym-norspermidine amides, having the following general formula:

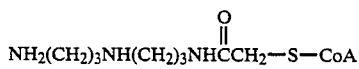

is prepared by attaching spermidine to coenzyme A via an acetic acid linkage.

It has been discovered that N-[2-(S-Coenzyme A)acetyl] sym-norsperimidine amide acts as a multisubstrate analog binding at the active site of spermidine/spermine acetyltransferase to inhibit acetylation of spermidine or spermine. When compared with known inhibitors, the present compound exhibits superior results. For example, sym-homo-sperimidine, putrescine and 1,3-diaminopropane also inhibit the acetylation of spermidine and spermine. The effectiveness of these compounds vary widely, with putrescine (the least effective) and 1,3-diaminopropane exhibiting marginal superiority to putrescine. The most potent inhibitor of these three known compounds is sym-homospermidine, which exhibits an order more effectiveness than the other two compounds. The novel compound of this invention inhibits the acetylation of spermidine or spermine by a factor of ten when compared to the most potent of the known inhibitors, (sym-homospermidine).

Furthermore, N-[2-(S-Coenzyme A) acetyl] sym-norspermidine is an effective agent that inhibits DNA replication and retards cell proliferation. For example, the present compound inhibits DNA replication and retards proliferation of rat hematoma and human prostate gland adenoma cells in culture. Marked retardation or arrest of tumor growth, often superior to that obtainable with cytotoxic drugs, has been demonstrated in several experimental tumor models. Additionally, sym-norspermidine in combination with cytotoxic drugs has lead to a more effective and tolerable combination regimen designed for clinical use.

Experimentation with murine tumors in which sym-norspermidine was studied alone and in combination with three different cytotoxic agents demonstrated that the effects of the sym-norspermidine derivative are superior to those of each cytotoxic drug and that the effects of any combination are synegistic.

The present invention contemplates employing the instant compound with other cytotoxic agents such as, for example, arabinosyl cytosine, bleomycin, cyclophosphamide and the like. Preferably, an effective dosage for the treatment of tumor related diseases range from about 10 mg to about 400 mg per kilogram of body weight per day, and such dosage units are employed so that a total of from about 700 mg to about 2.8 grams of the active compound for a subject of about 70 kg of body weight are administered in a 24-hour period. This dosage regimen can be adjusted to provide the optimum therapeutic response. For example, several divided doses can be administered daily or the dose can be proportionally reduced as indicated by the exigencies of the therapeutic situation. For example, in rats, prostate gland secretion is effectively inhibited and growth of the ventral prostate gland is significantly less than in the control group. Further, castrated rats treated with the novel compound show marked slowing of androgen-induced prostatic regrowth.

It has been found that N-[S-Coenzyme A) acetyl] sym-norsperimidine is an effective agent in prostatic hypertorphy, tumors and the "boggy" prostate gland syndrome. An effective dosage for the treatment of prostate related diseases range between 10 mg to about 400 mg per kilogram of body weight per day, and such dosage units are employed so that a total of from about 700 mg to about 2.8 grams of the active compound for a subject of about 70 kg of body weight are administered in a 24-hour period. This dosage regimen can be adjusted to provide the optimum therapeutic response. For example, several divided doses can be administered daily or the dose can be proportionally reduced as indicated by the exigencies of the therapeutic situation. For example, in rats, prostate gland secretion is effectively inhibited and growth of the ventral prostate gland is significantly less than in the control group. Further, castrated rats treated with the novel compound show marked slowing of androgen-induced prostatic regrowth.

The novel compound of the present invention is also effective as a contraceptive by inhibiting an enzyme that is critical for embryogenesis. For example, treated male and female mice prior to mating with untreated animals have shown to have no effect on fertility. However, when females were treated prior to copulation and treatment was continued for up to 18 days after fecundation, no effect was observed on implantation, but subsequent embryonic development was totally inhibited. Similar results have been shown in rats and rabbits. Interruption of gestation by inhibition of an enzyme whose activity is critical for embryogenesis constitutes an entirely novel approach to the possible interruption of early human pregnancy. Extrapolation from mice data indicates that the minimal susceptible period in human gestation would be 19 to 27 days following fertilization. An effective dosage for the interruption of human gestation ranges from about 10 mg to about 400 mg per kilogram of body weight per day, and such dosage units are employed so that a total from about 700 mg to about 2.8 grams of the active compound for a subject of about 70 kg of body weight are administered in a 24-hour period. This dosage regimen can be adjusted to provide the optimum therapeutic response. For example, several divided doses can be administered daily or the dose can be proportionally reduced as indicated by the exigencies of the therapeutic situation.

N-[2-(S-Coenzyme A) acetyl] sym-norspermidine is effective as a therapeutic agent in a select number of parasitic protozoan caused diseases. The compound inhibits the replication of *Trypanosoma brucei brucei*, (*T.b.brucei*) thereby completely eliminating the infection. *T.b. brucei* causes bovine trypansomiasis (Nagana) in cattle and *T.b. rhodesiene* and *T.b. gambiense* cause sleeping sickness in humans. Animal studies of malaria indicate that sym-norspermidine is an effective therapeutic agent against exoerythrocyctic infection. An effective dosage for the treatment of malaria range from about 10 mg to about 400 mg per kilogram of body weight per day, and such dosage units are employed so that a total of from about 700 mg to about 2.8 grams of the active compound for a subject of about 70 kg of body weight are administered in a 24-hour period. This dosage regimen can be adjusted to provide the optimum therapeutic response. For example, several divided doses can be administered daily or the dose can be proportionally reduced as indicated by the exigencies of the therapeutic situation.

Further, this compound is effective in treatment of *Pneumocystis carinii pneumonia*, an opportunistic parasitic protozoan caused infection in the setting of the Acquired Immune Deficiency Syndrome (AIDS). An effective dosage for the treatment of *pneumocystis carinii pneumoni* range from about 10 mg to about 400 mg per kilogram of body weight per day, and such dosage units are employed so that a total of from about 700 mg to about 2.8 grams of the active compound for a subject of about 70 kg of body weight are administered in a 24-hour period. This dosage regimen can be adjusted to provide the optimum therapeutic response. For example, several divided doses can be administered daily or the dose can be proportionally reduced as indicated by the exigencies of the therapeutic situation.

A decided practical advantage is that the active compound of the present invention can be administered in any convenient manner such as by the oral, intravenous, intramuscular, or subcutaneous routes.

The active compound can be orally administered, for example, with an inert diluent or with an assimilable edible carrier, or it can be enclosed in hard or soft shell gelatin capsule, or it can be compressed into tablets, or it can be incorporated directly with the food of the diet. For oral therapeutic administration, the active compound can be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations can, of course, be varied and can conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 100 mg and 4.0 grams of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, and/or dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulations.

The active compound can also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying techniques which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, "cancer disease" means blood malignancies such as leukemia, as well as other solid and non-solid malignancies such as the melanocarcinomas, lung carcinomas, and mammary tumors. The term "regression and palliation" means arresting or retarding the growth of the tumor or other manifestation of the disease compared to the course of the disease in the absence of treatment.

For a better understanding of the present invention together with other and further objects, reference is made to the following descriptions.

EXAMPLE I

Synthesis of N-[2-(S-Coenzyme A) acetyl] polyamine amides

Derivatives of sym-norspermidine, spermidine, sym-homospermidine, 1,3-diaminopropane and putrescine were produced by the method developed by Cullis, et al. (1982) for the synthesis of N-[2-(S-Coenzyme A) acetyl] spermidine amide. 2-(S-Coenzyme A) acetic acid thiophenyl ester in water was treated with excess spermidine or sym-norspermidine, sym-homospermidine, 1,3-diaminopropane and putrescine, and the pH was adjusted to 11 with aqueous sodium hydroxide (200 $\mu$mol). The solution was to stir at 4° C. for 16 h. under nitrogen. The crude reaction mixture was diluted with triethylammonium bicarbonate buffer (10 ml, 50 mM, pH 7.6) and applied to a column of DEAE-Sephadex equilibrated with this buffer at 4° C. The column was initially washed with 40 ml of triethylammonium bicarbonate buffer (pH 7.6), and the products were then eluted with a linear gradient of increasing buffer concentration (50–500 mM, pH 7.6) and the eluate collected in 3 ml fractions. Fractions comprising peaks of absorbance at 260 nm were pooled, concentrated and assayed for inhibitory activity. The active peaks were found to be ninhydrin reactive. The buffer salts were removed from the pooled active fractions by evaporation under reduced pressure. The residue was dissolved in water and stored frozen at −20° C. The purity of the derivatives were assessed by thin layer chromatography on cellulose plates (Whatman K2F) and developed in acetonitrile/2% acetic acid (1:1) or isobutyric acid/sodium isobutyrate, pH 4.3. Compounds were detected by reaction with ninhydrin and by u.v. absorbance. The Rf value in the former solvent of 2-(Coenzyme-A) acetic acid thiophenyl ester was 0.73, that of the sym-norspermidine amide was 0.59, and of the two spermidine derivatives were 0.51 and 0.59.

Extraction and assay of cytosolic and nuclear acetyltransferase activities

Cytosolic spermidine acetyltransferase activity was extracted from the livers of male Sprague-Dawley rats (weighing 200 to 350 grams) 6 h. after intraperitoneal injection of carbon tetrachloride (2 ml per kg), as described by Matsui, et al. (1981). The extract was kept frozen at −20° C. prior to use, and there was no activity loss after two weeks of storage. Spermidine acetyltransferase activity was assayed in a volume of 100 $\mu$l containing 100 $\mu$g of extract protein, 300 nmol spermidine, 0.8 nmol (40 nCi) [1$^{14}$C] acetyl Coenzyme A and 10 $\mu$mol tris-HCl (pH 7.8). The reaction was allowed to proceed at 30° C. for 10 min and was terminated by the addition of 20 $\mu$l of 1M NH$_2$OH.HCl. Protein was precipitated by boiling the samples for 3 min and was removed by centrifugation. 50 $\mu$l of the supernatant was applied to a 2.2 cm diameter disc of cellulose phosphate paper and was allowed to dry. The discs were washed in a beaker five times with water and three times with ethanol. The discs were then placed in 10 ml of scintillation fluid, and the radioactivity in them was assessed with a Beckman LS 3133T liquid scintillation spectrometer. The efficiency of this counting system was approximately 55%.

A crude nuclear acetyltransferase extract was prepared from the livers of untreated male Sprague-Dawley rats (weighing 200 to 350 g) by the method of Libby (1980). Approximately 650 $\mu$g of extract protein was used per assay. Histone acetyltransferase activity was assessed as in the cytosolic extract except that histones (270 $\mu$g per assay) were used as the acetyl acceptor, the reaction time was 5 min, and terminated reaction mixture was not centrifuged. The procedures for the assay of spermidine acetyltransferase activity in the nuclear extract were the same as in the cytosolic extract except that the reaction time was 5 min.

Non-enzymatic blank values for both histone and spermidine acetylation assays were routinely obtained by incubations of all the reactants excluding enzyme in the appropriate buffer. These values, which were always less than 7% of those observed when enzyme was present and were subtracted from all experimental values.

Chromatographic identification of the acetyltransferase reaction products

The reaction conditions were the same as those used in the above assay except that the reaction was terminated by the addition of an equal amount of 10% trichloroacetic acid. The samples were left at 4° C. for 2 h, and the protein was removed by centrifugation. Trichloroacetic acid was removed by three extractions with five volumes of ether. The resultant aqueous souution was applied to a 7×15 mm column of cellulose phosphate resin. The column was washed with 8 ml of 10 mM HCl and the acetylspermidine derivatives were eluted with 2 ml of 500 mM HCl. The eluate was taken to dryness and was redissolved in 50 $\mu$l distilled water and spotted on a strip of Whatman 3 MM paper. The paper was developed for 16 h. using 1-propanol/triethylamine/water (85:3:15) as a descending solvent system. The strips were dried and sliced into 3 cm sections and were placed in 20 ml of scintillation fluid. Radioactivity was assessed with a Beckman LS 3133T liquid scintillation spectrometer. Non-radioactive standard compounds were stained with a 0.5% ninhydrin solution in acetone.

Immunological techniques

Antiserum to rat liver spermidine/spermine $N^1$-acetyltransferase was obtained by immunizing a female New Zealand white rabbit with a homogeneous enzyme preparation, as described by Della, et al. (1982). The rabbit was immunized by multiple site intradermal injections using 45 μg of the protein emulsified in Freund's complete adjuvant. A booster injection of 25 μg in incomplete adjuvant was given at 6 weeks and antiserum was collected two weeks later.

Immunoprecipitation of acetylase activity was carried out by incubation of the sample in a total volume of 0.11 ml containing 50 mM Tris—HCl, pH 7.5, 1% bovine serum albumin, 1 mM spermidine and 0.02% Brij 35 and the antiserum at 4° C. overnight. After this incubation 25 μl of bacterial protein A adsorbant (Miles Laboratories, Elkhart, Ind.) was added, and after a further incubation of 90 min at 4° C., the solution was centrifuged at 15,000 ×g for 1 min. The supernatant was then tested for acetylase activity.

As shown by FIG. 1 sym-norspermidine is a very potent inhibitor of the acetylation of spermidine by crude cytosolic extracts from livers of carbon tetrachloride treated rats and by highly purified spermidine/spermine $N^1$-acetyltransferase. A full kinetic analysis was not carried out, but the inhibition was greater when the assays were carried out at lower concentrations with either substrate.

Figure 2A:
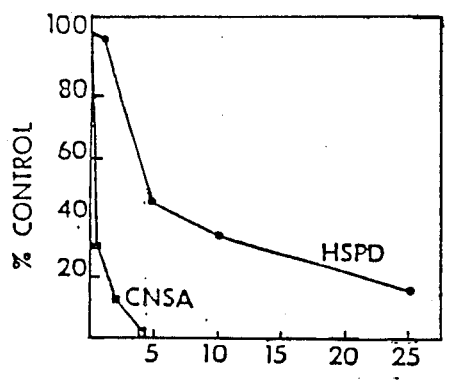
FIG. 2 is a graphic illustration depicting the inhibition of spermidine/spermine $N^1$-acetyl-transferase by N-[2-(S-Coenzyme A)acetyl] polyamine amides. A illustrates the inhibition by N-[2-(S-Coenzyme A) acetyl] amides of sym-norspermidine. B illustrates the inhibition by the N-[2-(S-Coenzyme A) acetyl] amides of spermidine. C illustrttes the inhibition by the N-[2-(S-Coenzyne A) acetyl] amides of putrescine and 1,3-diaminopropane and by 2-(S-Coenzyme A) acetic acid thiophenyl ester.
Figure 2B:
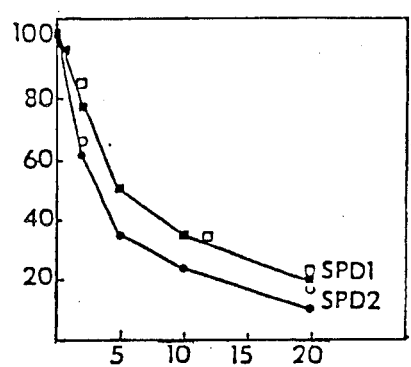

Similar derivatives were prepared from spermidine, sym-homospermidine, 1,3-diaminopropane and putrescine and these derivatives were tested for inhibitory activity towards spermidine/spermine $N^1$-acetyltransferase (FIG. 2). The products from the reaction of 2-(S-Coenzyme A) acetic acid thiophenyl ester with spermidine was separated into 2 peaks on DEAE-Sephadex chromatography. These derivatives could also be separated by thin layer chromatography and were designated I and II in accordance with their retention on DEAE-Sephadex. The two derivatives differed slightly in their ability to inhibit the spermidine/spermine $N^1$-acetyltransferase (FIG. 2). It is likely that they represent amides at the $N^1$- and $N^8$-position of spermidine, respectively, although they were not fully characterized. The spermidine amides are strong inhibitors of the $N^1$-acetyltransferase, but are more than an order of magnitude less potent than the sym-norspermidine derivative. Similarly, according to FIG. 2A the sym-homospermidine derivative is ten times less active than the sym-norspermidine compound.

Figure 2C:
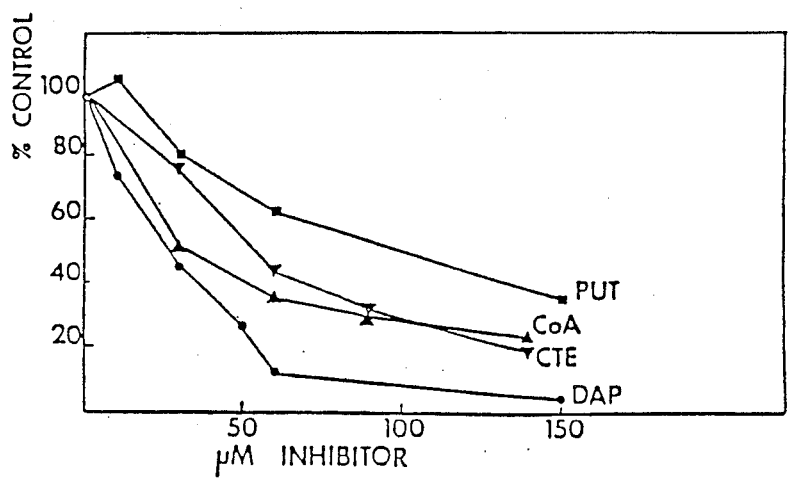

The amides derived from 1,3-diaminopropane and putrescine are much less active then the amide derived from 1,3-diaminopropane, which is marginally more inhibitory than coenzyme A (See FIG. 2C). These results are consistent with the known properties of spermidine/spermine $N^1$-acetyltransferase and the concept that these inhibitors act as multisubstrate analogs.

Thus, while the invention has been described with reference to certain preferred embodiments, those skilled in the art will realize that changes and modifications may be made thereto without departing from the full and intended scope of the appended claims.

What is claimed is:

1. A compound having the formula

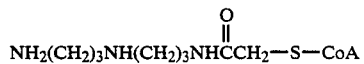

and the pharmacologically acceptable acid addition salts thereof.

2. A pharmaceutical composition comprising the compound having the formula

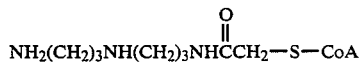

and a pharmaceutically acceptable carrier.

3. A pharmaceutically acceptable composition in daily dosage form containing from about 10 mg to about 400 mg per kilogram of body weight of a composition of claim 2.

* * * * *

UNITED STATES PATENT AND TRADEMARK OFFICE
CERTIFICATE OF CORRECTION

PATENT NO. : 4,826,968

DATED : May 2, 1989

INVENTOR(S) : Anthony E. Pegg, et al.

It is certified that error appears in the above-identified patent and that said Letters Patent is hereby corrected as shown below:

Column 2, line 61: "A illustrates" should read as --Panel A illustrates--

Column 2, line 63: "B illustrates" should read as --Panel B illustrates--.

Column 2, line 65: "C illustrttes" should read as --Panel C illustrates--.

Column 5, line 29: "pneumoni" should read as --pneumonia--.

Column 8, line 15: "[1$^{14}$C]" should read as --[1-$^{14}$C]--.

Column 8, line 18: "1M NH$_2$OH.HCl." should read as --1 M NH$_2$OH·HCl.--.

Column 8, lines 58-59: "souu-tion" should read as --solu-tion--.

Signed and Sealed this

Seventh Day of August, 1990

Attest:

HARRY F. MANBECK, JR.

*Attesting Officer*          *Commissioner of Patents and Trademarks*